United States Patent [19]

Burke, Jr. et al.

[11] Patent Number: 5,200,546
[45] Date of Patent: Apr. 6, 1993

[54] PHOSPHONOALKYL PHENYLALANINE COMPOUNDS SUITABLY PROTECTED FOR USE IN PEPTIDE SYNTHESIS

[75] Inventors: Terrence R. Burke, Jr., Bethesda; Benjamin B. Lim, Baltimore, both of Md.

[73] Assignee: The United States of America as represented by the Department of Health and Human Services, Washington, D.C.

[21] Appl. No.: 767,621

[22] Filed: Sep. 30, 1991

[51] Int. Cl.$^5$ .................. C07F 9/40; C07F 9/6518; C07F 9/572
[52] U.S. Cl. .................. 558/190; 548/113; 548/413; 558/178; 558/179; 558/193
[58] Field of Search .............. 558/190, 413, 113

[56] References Cited

U.S. PATENT DOCUMENTS 4,657,899  4/1987  Rzeszotarski .............. 514/120

FOREIGN PATENT DOCUMENTS 2198134  6/1988  United Kingdom .............. 558/190

OTHER PUBLICATIONS

Paquet, A. *Can. J. Chem.* 1982, 60, 976–980.
Banert, K. *Tetrahedron Lett.* 1985, 26(43), 5261–5264.
Carey, F. A. et al. *Advanced Organic Chemistry;* Second edition; Plenum: New York, 1983; p. 193.
Streitwieser, A. et al. *Introduction of Organic Chemistry;* Third edition; Macmillan: New York, 1985; pp. 737–738.

*Primary Examiner*—Mary C. Lee
*Assistant Examiner*—Michael G. Ambrose
*Attorney, Agent, or Firm*—Birch, Stewart, Kolasch & Birch

[57] ABSTRACT

There are disclosed novel compounds of the formula:

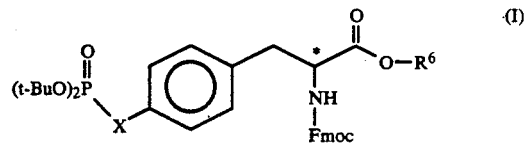

wherein,
x is —$CH_2$—, —CHF—, —$CF_2$, —CHOH— or —C(O)—;
$R^6$ is hydrogen, benzyl, pentafluorophenyl, nitrophenyl, 1-benzotriazolyl or 1-succinimidoyl;
Fmoc is 9-fluorenylmethyloxycarbonyl; and
* indicates a chiral carbon atom.

The Formula (I) compounds are useful in synthesizing peptides. There are also disclosed novel synthesis methods which include the step of hydrogenating a compound of the Formula

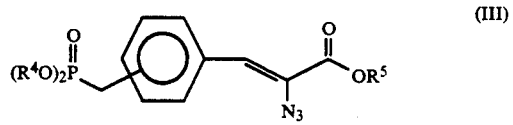

wherein $R^4$ and $R^5$ are $C_{1-8}$ lower alkyl, to give a compound of the formula

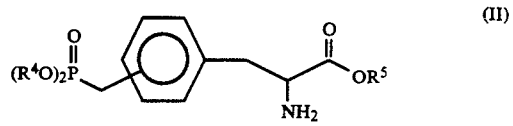

wherein $R^4$ and $R^5$ are as defined above. The compounds of formula (II) are useful as intermediates in preparing certain formula (I) compounds.

5 Claims, No Drawings

PHOSPHONOALKYL PHENYLALANINE COMPOUNDS SUITABLY PROTECTED FOR USE IN PEPTIDE SYNTHESIS

FIELD OF THE INVENTION

The present invention is concerned with providing phosphonic acid-containing derivatives of phenylalanine and optically active isomers thereof, which are functionalized in a manner which makes them suitable for facile incorporation into peptides using standard solid-phase or solution-phase techniques.

BACKGROUND OF THE INVENTION

Synthesis of 4-phosphonomethyl-DL-phenylalanine (Formula 1a), and derivatives thereof (Formulas 1b–d) have previously been reported [1-4] (See Table 1). The purposes of such preparations were to utilize the prepared 4-phosphonomethyl-DL-phenylalanines as competitive antagonist of N-methyl-D-aspartic acid[2] or as mimics of O-phosphotyrosine [1,3,4]. These previously prepared derivatives are not suitable for facile incorporation into peptides or peptide mimetics using standard protocols developed for either solution-phase or solid-phase peptide synthesis using "Fmoc protocols" [5,6].

Central to peptide synthesis is the protection of reactive functional groups with moieties which are easily removed under conditions which are compatible with the preservation of other functionalities in the peptide. A major branch of peptide chemistry has recently evolved using 9-fluorenylmethyloxycarbonyl (Fmoc) groups for protection of α-amino groups during coupling reactions of amino acid monomers into peptide chains. The Fmoc groups are then generally removed by brief treatment with an appropriate base such as piperidine. In such reactions, other chemically reactive groups on the amino acid monomers must be protected by functionalities which are stable to the basic conditions utilized to remove Fmoc groups. Traditionally, these other groups were removed by mild acid treatment (e.g., trifluoroacetic acid) such as used to cleave the finished peptide from a given resin. The tert-butyl group is used widely in Fmoc-bearing residues for the protection of hydroxyl groups, since it is stable to base and easily removed by mild acid treatment. Unlike the present inventive compounds, the prior known 4-phosphonomethyl-DL-phenyl-alanine compounds shown in Table 1 (Compounds 1a–1d) require significant synthetic manipulation to render them suitable for peptide synthesis.

TABLE 1

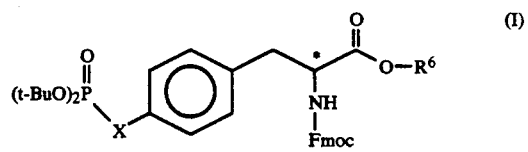

| | $R^1$ | $R^2$ | $R^3$ | Ref |
|---|---|---|---|---|
| 1a | H | H | OH | 1, 2, 3, 4 |
| 1b | Et | Bz[a] | OH | 1 |
| 1c | Et | Ac | OMe | 2 |
| 1d | H | H | HNBn[b] | 4 |

[a]Bz = benzoyl
[b]Bn = benzyl

SUMMARY OF THE INVENTION

The present invention provides novel 4-phosphonomethyl-DL-phenylalanine derivatives, analogues thereof and optical isomers thereof of the following formula:

(I)

wherein t-BuO represents tertiary butoxy, Fmoc represents 9-fluorenylmethyloxycarbonyl, X is $-CH_2-$, $-CHF-$, $-CF_2-$, $-CHOH-$ or $-C(O)-$, $R^6$ is hydrogen, benzyl, pentafluorophenyl, nitrophenyl, 1-benzotriazolyl, and 1-succin-imidoyl, and * indicates a chiral carbon atom.

The compounds of Formula (I) are useful in peptide synthesis. More particularly, they are useful in preparing peptides wherein one wishes to obtain stable analogues of O-phosphotyrosine which are useful as molecular tools in biochemical studies and/or as therapeutic agents in the treatment of certain proliferative diseases.

The present invention is also concerned with providing a novel synthesis process wherein an azide derivative of Formula III is converted into the corresponding amine derivatives of Formula II, as shown in the following Reaction Scheme I.

Reaction Scheme I

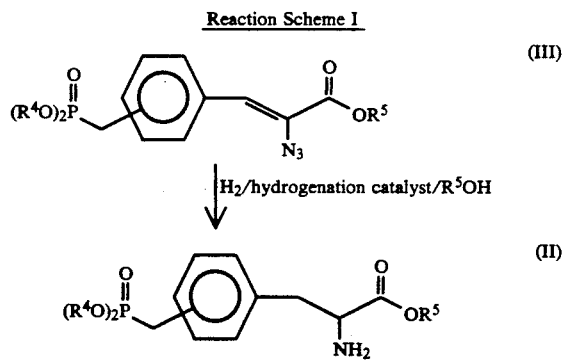

In the above Reaction Scheme I, $R^4$ and $R^5$ are the same or different and are selected from the group consisting of $C_{1-8}$ lower alkyl (e.g., methyl, ethyl, propyl, 2-propyl, butyl, t-butyl, and the like), and the hydrogenation catalyst is 10% Pd.C, or platinum, or the like. The compounds are useful as intermediates in forming certain of the Formula I compounds discussed herein.

The present invention is also concerned with another novel synthesis process which may be used in preparing certain compounds of Formula I, and certain related derivatives. This synthesis process is shown below in Reaction Scheme II, and encompasses as one of its steps the synthesis process outlined in Reaction Scheme I.

Reaction Scheme II.

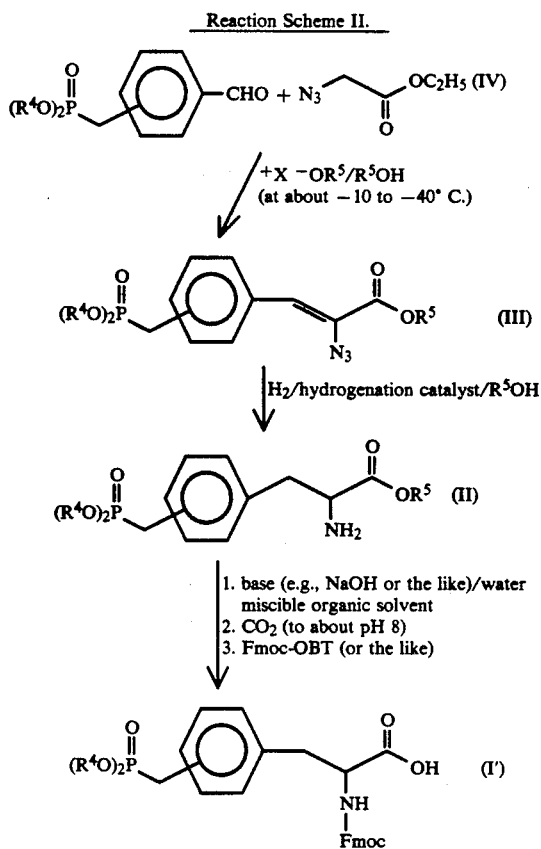

In the above Reaction Scheme (II), $R^4$ and $R^5$ are $C_{1-8}$ lower alkyl (e.g., methyl, ethyl, propyl, butyl, penyl, hexyl, octyl, 2-propyl, t-butyl, and the like), $X^+$ is an alkali metal such as sodium or the like; the hydrogenation catalyst is 10% Pd.C, platinum or the like, the water miscible organic solvent is dioxane, an alcohol (e.g., methanol, ethanol, etc.), acetyl nitrile or the like, Fmoc-OBT is 1-benzotriazolyl-9-fluorenylmethyloxy carbonate, and Fmoc is 9-fluorenylmethyloxycarbonyl. The compound 1-succin-imidoly-9-fluorenylmethyl carbonate, or another suitable compound which is capable of releasing a Fmoc group, may be used in the above reaction scheme in place of Fmoc-OBT, if so desired.

The compounds of Formula (I') shown in Reaction Scheme II above may be reacted with an appropriate $R^6$ moiety to form the analogous Formula (I) compound wherein $R^6$ is other than hydrogen. Such reactions are readily known by those skilled in the art and include, for example, reacting a Formula I' compound with carbonyldiimidazole (DCC) prior to reacting the same with an appropriate $R^6$ moiety.

DETAILED DESCRIPTION OF THE INVENTION

The following description and Example sections are provided to further aid those desiring to practice the present invention. Even so, the following sections are not to be construed as limiting to the scope of protection afforded to the present inventors in their discoveries.

The present invention is concerned with providing compounds of Formula (I) above for use, for example, in peptide synthesis. Such compounds of Formula (I) can be obtained as shown in the above Reaction Scheme (II) or as otherwise discussed herein. As a specific example of the synthesis of a Formula (I) compound, the following synthesis is provided.

4[Bis(t-butyl)phosphonomethyl]-N-Fmoc-DL-phenylalanine

Synthesis Overview

Central to the synthesis of the title compound (compound No. 4 in the synthesis below) is the aldol condensation of ethyl α-azidoacetate[7] with 4-[bis(tert-butyl)-phosphonomethyl]-benzaldehyde (compound 1) to yield vinyl azide (compound No. 2) (74%)). The vinyl azide (compound No. 2) is key to the synthetic route as the tert-butyl groups thereof are retained under the mild conditions (2.8 bar $H_2$/10% Pd.C) and employed to effect transformation to the amino ester (compound No. 3). Finally, hydrolysis of the methyl ester with concomitant introduction of the Fmoc-amino protection to yield compound No. 4 is achieved by sequentially treating compound 3 with 1 N sodium hydroxide (20 min.) and thereafter adjusting the pH to 8 by introducing carbon dioxide and allowing the mixture to react overnight with 1-benzotriazolyl-9-fluorenyl-methyl carbonate (Fmoc-OBT).[8] The final product (compound No. 4) is obtained as a white powder (48% overall yield).

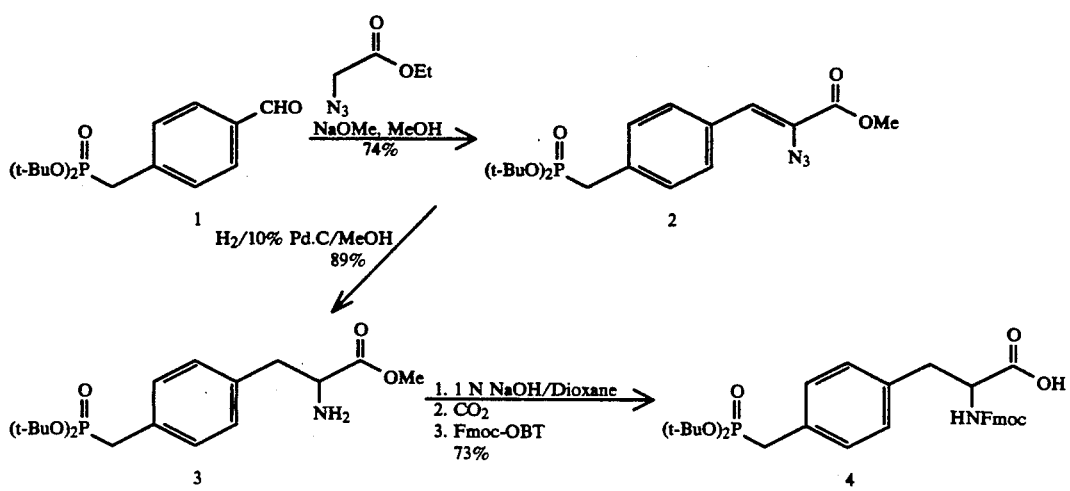

Compound Preparation

α-Azido-4-[bis(tert-butyl)phosphonomethyl]cinnamic acid methyl ester (Compound No. 2)

To a cold (−30° C.) solution of 4-[bis(tert-butyl)-phosphonomethyl]benzaldehyde (compound No. 1, 3.12 g, 10 mmol) and ethyl α-azidoacetate (12.90 g, 100 mmol, 10 equiv) in anhydrous MeOH (50 mL) is added a solution of 5.4 M NaOMe (14.8 mL, 80 mmol, 8 equiv) over 2 minutes under argon with stirring. The colorless reaction mixture is stirred at 2° C. for 1 hour, then diluted with brine (300 mL); extracted with Et$_2$O (3×100 mL); dried (MgSO$_4$) and Et$_2$O removed. The resulting colorless oil is dissolved in pet.ether (30 mL), cooled to −78° C., then warmed to 0° C. with mixing to yield a white crystalline solid. The solid is treated with ice-cold pretroleum ether/Et$_2$O (30:1, 30 ml), filtered and dried; yield 2.86 g (74%); mp 109°-111° C. C$_{19}$H$_{28}$N$_3$O$_5$P MW 409 (compound is too unstable for combustion analysis).

FABMS:m/z=410 (M+1).

IR (KBr) v=2980, 2124, 1707, 1439, 1369, 1330 cm$^{-1}$.

$^1$H-NMR (200 MHz, CDCl$_3$):δ=1.42 (s, 18 H, 2t-C$_4$H$_9$), 3.05 (d, 2 H, J=22 Hz, P-CH$_2$), 3.90 (s. 3 H, OCH$_3$), 6.90 (s, 1 H, vinylic), 7.28 (dd, 2 H, J=2 Hz and 8 Hz, ArH$_3$ and $_5$), 7.74 (d, 2 H, J=8 Hz, Arh$_2$ and $_6$).

4-[Bis(tert-butyl)phosphonomethyl]-D,L-phenylalanine methyl ester (Compound No. 3)

A solution of compound 2 (4.50 g, 110 mmol) in MeOH (30 mL) is shaken in a Parr apparatus (2.8 bar H$_2$) over 10% Pd.C (1.10 g) for 1 hour at room temperature. Filtration through Celite filter and removal of solvent yields compound No. 3 as an oil: 3.75 g (89%).

| C$_{19}$H$_{32}$NO$_5$P.½H$_2$O | calc. | C 57.20 | H 8.46 | N 3.51 |
|---|---|---|---|---|
| (385) | found | C 57.23 | H 8.14 | N 3.55 |

FABMS: m/z=386 (M+1)

IR (film) v=3853, 3383, 2979, 1739, 1653, 1558, 1540, 1514, 1456, 1394, 1369 cm$^{-1}$.

$^1$H-NMR (250 MHz, CDCl$_3$):δ=1.42 (s, 18 H, 2t-C$_4$H$_9$), 1.66 (br s, 2 H, NH$_2$), 2.86 (dd, 1 H,J=8 Hz and 13 Hz, H$_{\beta1}$), 3.01 (d,2 H, J=21 Hz, P-CH$_2$), 3.06 (dd, 1 H, J=5 Hz and 13 Hz, H$_{\beta2}$), 3.70 (s, 3 H, OCH$_3$), 3.72 (dd, 1 H, J=5 Hz and 8 Hz, H$_\alpha$), 7.11 (d, 2 H, J=8 Hz, ArH$_2$ and $_6$), 7.22 (dd, 2 H, J=2 Hz and 8 Hz, ArH$_3$ and $_5$. Structural assignments were supported by $^{13}$C-NMR and DEPT experi-ments.

4-[Bis(tert-butyl)phosphonomethyl]-N-Fmoc-DL-phenylalanine (Compound No. 4)

A solution of amine compound No. 3 (770 mg, 1.93 mmol) in dioxane (10 mL) is stirred at room temperature (20 min) with aqueous 1 N NaOH (10 mL, 10 mmol, 5 equiv). Carbon dioxide is then bubbled in (resulting pH =8.0-8.5) and Fmoc-OBT (857 mg. 2.40 mmol, 1.2 equiv) is added as a suspension in dioxane (3×10 mL) and stirred overnight at ambient temperature. The reaction mixture is partitioned between cold aqueous 5% citric acid (200 mL) and CHCl$_3$ (3×100 mL); the combined organic is washed with cold 5% citric acid (1×100 mL); brine (1×200 mL); dried (MgSO$_4$) and taken to dryness, yielding a light yellow resin (1.92 g). The resin is taken up in CHCl$_3$ and filtered through a silica pad. Unreacted Fmoc-OBT and faster impurities are removed with CHCl$_3$ (5×100 mL) with product then being eluted (8 ×100 mL); 1% EtOH in CHCl$_3$ and taken to dryness, providing a foam (953 mg) which is dissolved in Et$_2$O (5 mL) and cooled with petroleum ether (20 mL) to yield compound No. 4 as a white powder: 835 mg (73%); mp 65°-70° C. (gas, dec.).

| C$_{33}$H$_{40}$NO$_7$P | calc. | C 66.77 | H 6.79 | N 2.36 |
|---|---|---|---|---|
| (593) | found | 67.08 | 7.26 | 2.32 |

FABMS:m/z=594 (M+1).

IR (film) v=2979, 1721, 1513, 1450, 1370 cm$^{-1}$.

$^1$H-NMR (250 MHZ, CDCl$_3$):δ=1.31 (s, 9 H,t-C$_4$H$_9$), 1.38 (s, 9 H,t-C$_4$H$_9$), 3.01 (dd, 1 H, J=14 Hz and 22 Hz, P-C-H$_\alpha$), 3.13 (dd, 1 H, J=14 Hz and 22 Hz, P-C-H$_\beta$), 3.18 (M, 1 H, H$_{\delta1}$), 3.29 (m, 1 H, H$_{\beta2}$), 4.22 (t, 1 H, J=7 Hz, OC-H), 4.32 (dd$^a$, 1 H, J=7 Hz and 10 Hz, NCO2C-H$_\alpha$), 4.48 (dd$^a$, 1 H, J=7 Hz and 10 Hz, NCO2C-H$_\beta$), 4.68 (m, 1 H, NC-H), 5.40 (d, 1 H, J=7 Hz, N-H), 7.12 (d, 2 H, J=8 Hz, ArH$_2$ and $_6$), 7.20 (dd, 2 H, J=2 Hz and 8 Hz, ArH$_3$ and $_5$), 7.30 (dt$^b$, 2 H, J=4 Hz and 7 Hz, fluor.-H$_2$ and $_7$$^c$, 7.39 (t$^b$, 2 H, J=7 Hz, fluor.-H$_3$ and $_6$$^e$, 7.59 (br dd$^a$, 2 H, J=4 Hz and 7 Hz, fluor.-H$_4$ and $_5$)$^d$, 7.76 (bt d, 2 H, J=7 Hz, fluor.-H$_1$ and $_8$)$^d$. Structural assignments were supported by $^1$H-$^1$HCOSY and $^{13}$C-MNR.

$^a$ coupling pattern is distorted;
$^b$ coupling pattern is apparent;
$^c$ assignments may be reversed; and
$^d$ assignments may be reversed.

Optical Isomers

It is expected that compounds (e.g., peptides) prepared using the D and L optical isomers of the Formula I compound, will exhibit different biological interactions with biological systems. The preparation of Formula (I) D and L isomers can typically be achieved by resolution of a mixture diasteriomeric salts formed by reaction of either the free acid (with or without Fmoc-protection of the α-amino group), with a chiral amine or by reaction of the free acid (without Fmoc-protection of the α-amino group) with a chiral acid. For example, resolution of N-acetyl-DL-tyrosine as the brucine salt typifies such procedures. [9]

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and/or patents referred herein is expressly incorporated herein by reference in its entirety.

REFERENCES

1. Marseigne, I.; Roques, B. P. Synthesis of new amino acids mimicking sulfated and phosphorylated tyrosine residues. J. Org. Chem., 1988, 53, 3621-3624.
2. Bigge, C. F.; Drummond, J. T.; Johnson, G.; Malone, T.; Probert, A. W., Jr.; Marcoux, F. W.; Coughenour, L. L.; Brahce, L. J. Exploration of phenyl-spaced 2-amino-(5,9)-phosphonoalkanoic acids as competitive N-methyl-D-aspartic acid antagonists. J. Med. Chem., 1989, 32, 1580-1590.
3. Bayle-Lacoste, M.; Moulines, J.; Collignon, N.; Boumekouez, A.; de Tinguy-Moreaud, E.; Neuzil, E. Synthesis of 4-phosphono-DL-phenylalanine and of 4-(phosphonomethyl)-DL-phenylalanine, two analogues of O-phosphotyrosine. Tetrahedron, 1990, 46, 7793-7802.
4. Roques, B. P.; Marseigne, I.; Charpentier, B. Preparation of amino acids and tyrosine-containing peptides as drugs and pharmaceutical compositions containing them. Eur. Pat. Appl. EP 354 108 (CA 113:78979x), 1990.
5. Carpino, L. A.; Han, G. Y. The 9-fluorenylmethoxycarbonyl function, a new base-sensitive amino-protecting group, J. Amer. Chem. Soc., 1970, 92, 5748-5749.
6. Burke, T. R.; Knight, M.; Chandrasekhar, B. Solid-phase synthesis of viscosin, a cyclic depsipeptide with antibacterial and antiviral properties. Tetrahedron Letters, 1989, 30, 519-522.
7. Hemetsberger, H.; Knittel, D.; Weidmann, H. Monatsh. Chem., 1969, 100, 1599-1603.
8. Paquet, A. Can. J. Chem., 1982, 60, 976-80.
9. Sealock, R. R. D-Tyrosine in Biochemical Preparations, Vol. I, John Wiley & Sons, Inc., London, England, (H. E. Carter, Ed.), 1949, 71-74.

What is claimed is:

1. A compound of the formula:

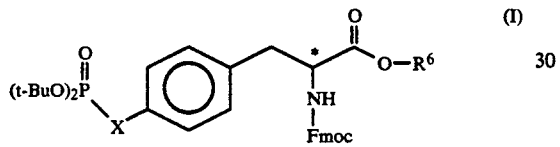

wherein x is —CH$_2$—, —CHF—, —CF$_2$—, —CHOH— or —C(O)—, t-BuO is tertiary butoxy, Fmoc is 9-fluorenylmethyloxycarbonyl; R$^6$ is hydrogen, pentafluorophenyl, nitrophenyl, benzotriazolyl or succinimidolyl, and * indicates a chiral carbon atom; and the optical isomers thereof.

2. The compound of claim 1, which is 4-(bis(tert-butyl)phosphonomethyl)-N-Fmoc-DL-phenylalanine.

3. The compound of claim 1, which is 4-(bis(tert-butyl)phosphonomethyl)-N-Fmoc-D-phenylalanine.

4. The compound of claim 1, which is 4-(bis)(tert-butyl)phosphonomethyl)-N-Fmoc-L-phenylalanine.

5. A process for preparing a compound of formula (I'):

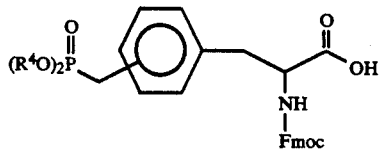

wherein R$^4$ is C$_{1-8}$ lower alkyl and Fmoc is 9-fluorenylmethyloxycarbonyl; the process comprising the steps of:

Step 1—reacting a compound of formula (IV)

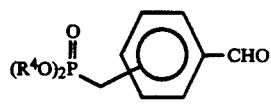

wherein R$^4$ is as defined above, with ethyl α-azidoacetate in the presence of an alkali metal, and an alcohol solvent of the formula R$^5$OH, wherein R$_5$ is C$_{1-8}$ lower alkyl, to give a compound of formula (III)

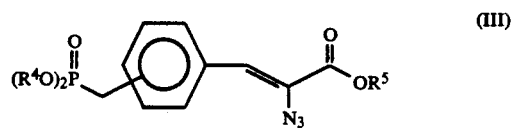

wherein R$^4$ and R$^5$ are as defined above;

Step 2—hydrogenating the formula (III) compound prepared in Step 1 to give a compound of Formula (II)

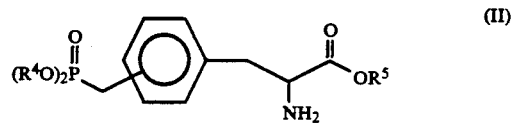

wherein R$^4$ and R$^5$ are as defined above; and

Step 3—reacting the formula II compound prepared in Step 2 with an appropriate base, adjusting the reaction mixture to about pH 8 and thereafter reacting the Formula (II) compound with 1-benzotriazolyl-9-fluorenylmethyl carbonate or 1-succinimidoly-9-fluorenylmethyl carbonate.

* * * * *